(12) United States Patent
Kim et al.

(10) Patent No.: US 9,325,147 B2
(45) Date of Patent: Apr. 26, 2016

(54) METHOD AND APPARATUS FOR GENERATING LASER

(75) Inventors: Deog Yong Kim, Cheongju (KR); Sang Do Kim, Daejeon (KR)

(73) Assignee: GTC CO., LTD., Daejeon (KR)

( * ) Notice: Subject to any disclaimer, the term of this patent is extended or adjusted under 35 U.S.C. 154(b) by 178 days.

(21) Appl. No.: 14/004,526

(22) PCT Filed: Mar. 9, 2012

(86) PCT No.: PCT/KR2012/001720
§ 371 (c)(1),
(2), (4) Date: Nov. 27, 2013

(87) PCT Pub. No.: WO2012/124936
PCT Pub. Date: Sep. 20, 2012

(65) Prior Publication Data
US 2014/0081171 A1    Mar. 20, 2014

(30) Foreign Application Priority Data

Mar. 11, 2011 (KR) .................. 10-2011-0021622

(51) Int. Cl.
*A61B 5/00* (2006.01)
*H01S 3/10* (2006.01)
*A61B 5/15* (2006.01)
*A61B 5/151* (2006.01)
*A61B 18/20* (2006.01)

(52) U.S. Cl.
CPC ............... *H01S 3/10* (2013.01); *A61B 5/1411* (2013.01); *A61B 5/150022* (2013.01); *A61B 5/15138* (2013.01); *A61B 5/150954* (2013.01); *A61B 18/20* (2013.01)

(58) Field of Classification Search
CPC ...... A61B 5/1411; A61B 5/1405; A61B 5/15; A61B 5/150053; A61B 5/150022; A61B 5/15138; H01S 3/10
See application file for complete search history.

(56) References Cited

U.S. PATENT DOCUMENTS 5,643,252 A * 7/1997 Waner ................. A61B 5/1411
                                                        604/21
6,074,383 A * 6/2000 Grippi .................... A61B 18/20
                                                        606/1
6,733,493 B2   5/2004 Gruzdev et al.
(Continued)

FOREIGN PATENT DOCUMENTS

CN      1553787 A    12/2004
CN    101437452 A     5/2009
(Continued)

*Primary Examiner* — Max Hindenburg
(74) *Attorney, Agent, or Firm* — Drinker Biddle & Reath LLP

(57) ABSTRACT

Disclosed herein is an apparatus for generating a laser. The apparatus includes, on an upper surface of a PCB, a display unit (50) which displays a charge state and an intensity of laser, a switch unit (60) which control power, the intensity of the laser and the emission of the laser, a safety unit (80) which includes contact point parts, and a control unit (70). The apparatus includes, on a rear surface of the PCB, a reflector (10) which has first and second spaces, a xenon tube (12) which emits light, a crystal rod (11) which amplifies the light to generate a laser, a focusing lens (15) which focuses the laser and forms a focus, a focusing lens installation part (13), a capacitor (20) which applies voltage to the xenon tube, a drive unit (90) which charges the capacitor, and a battery (30) which supplies power to the drive unit.

10 Claims, 9 Drawing Sheets

(56) References Cited

U.S. PATENT DOCUMENTS

| | | | |
|---|---|---|---|
| 7,577,179 B2 * | 8/2009 | Nishida | H01S 3/025 372/101 |
| 7,976,478 B2 * | 7/2011 | Fujiwara | A61B 5/14 600/573 |
| 8,357,106 B2 * | 1/2013 | Kusaka | A61B 5/1411 600/583 |
| 8,394,085 B2 | 3/2013 | Horikawa et al. | |
| 8,439,848 B2 * | 5/2013 | Nishida | A61B 5/1411 600/583 |
| 8,529,472 B2 * | 9/2013 | Matsumura | A61B 5/1411 600/583 |
| 2010/0030110 A1 | 2/2010 | Choi et al. | |
| 2010/0100007 A1 | 4/2010 | Sakamoto | |

FOREIGN PATENT DOCUMENTS

| | | |
|---|---|---|
| JP | 2008-194345 A | 8/2008 |
| KR | 10-2007-0102208 A | 10/2007 |
| KR | 10-2008-0103542 A | 11/2008 |
| WO | 2007/119900 A1 | 10/2007 |

* cited by examiner

METHOD AND APPARATUS FOR GENERATING LASER

TECHNICAL FIELD

The present invention relates, in general, to apparatuses for generating lasers and, more particularly, to a laser generating apparatus and method which generates an Er:YAG laser to be used in blood collection.

BACKGROUND ART

Generally, blood collection devices are used to collect blood from human bodies, for example, a blood sample used for a blood test. Particularly, diabetic patients mainly use such blood collection devices. Most diabetic patients use lancing devices for blood collection. Lancing devices are used in such a way as to lance the skin of with a sharp needle and cut capillary vessels. Disadvantages of such lancing devices for blood collection are as follows: the skin of the patient must be lanced and a callus is thus formed at the lanced portion; as a callus is formed, a depth to which the needle enters the skin of the patient must be gradually increased; and it is required to replace the needle with a new one every time. Particularly, a bigger problem is that if the needle is reused without replacement, there is the probability of a secondary injection being caused. Furthermore, because a needle is used for blood collection, patients suffer from pain and fear of the needle.

In an effort to overcome the above disadvantages and affection risk, a laser blood collection device was proposed. However, although the laser blood collection device can solve problems in sanitation and overcome a disadvantage of a patient suffering from pain, there is a problem in that due to structural characteristics, the size thereof is increased, making it difficult to carry.

Moreover, a laser generating apparatus is configured such that laser is emitted only by pushing an emission button. If children touch the laser blood collection device, a dangerous situation may be induced. Therefore, particular attention is required.

DISCLOSURE

Technical Problem

Accordingly, the present invention has been made keeping in mind the above problems occurring in the prior art, and an object of the present invention is to provide an apparatus and method for generating a laser which is able to solve the conventional sanitation problem and reduce pain during blood collection.

Another object of the present invention is to provide an apparatus and method for generating a laser which is reduced in size to increase the portability thereof and is able to resist water.

A further object of the present invention is to provide an apparatus and method for generating a laser which includes an accident prevention structure, thus markedly enhancing safety.

Technical Solution

In order to accomplish the above objects, in an aspect, the present invention provides a apparatus for generating a laser, including: on an upper surface of a PCB, a display unit displaying a battery charge state and an intensity of a laser; a switch unit provided to turn power on/off, adjust the intensity of the laser and control emission of the laser; a safety unit comprising first through third contact point parts; and a control unit controlling the drive unit and the display unit, and on a rear surface of the PCB, a reflector having a first space and a second space therein; a xenon tube emitting light in the first space; a crystal rod amplifying the light in the second space and generating a laser; a focusing lens focusing the laser and forming a focus; a focusing lens installation part in which the focusing lens is installed; a capacitor applying voltage to the xenon tube; a drive unit charging the capacitor; and a battery supplying power to the drive unit.

The xenon tube and the crystal rod may be provided in the reflector and oriented perpendicular to or parallel to the rear surface of the PCB.

An inner surface of the reflector may be plated with chrome.

The PCB in contact with an inner surface of the reflector may be plated with gold.

The display unit may be embodied by at least one selected from among an LED, an LCD and an OLED.

The first through third contact point parts of the safety unit may respectively make contact with first through third contact parts of a casing.

The switch unit may include: a power button used to turn on or off the laser generating apparatus; a selection button used to select a level of laser intensity; and a laser emission button used to conduct blood collection.

Blood collection may be conducted in such a way that one hand of a user makes contact with the third contact part, and the first and second contact parts are brought into contact with a target portion of a body (skin) of the user.

Blood collection may be conducted in such a way that one hand of a user makes contact with the third contact part, the other hand of the user makes contact with a body of a patient (another person), and the first and second contact parts are brought into contact with a target portion of the body of the patient.

The apparatus may further include, on a rear surface of the casing, a charging jack connector used to charge the battery.

In another aspect, the present invention provides a method for generating a laser, including turning on power; charging a capacitor using a drive unit; selecting a level of laser emission and adjusting an intensity of a laser; checking a charge state of the capacitor using a display unit; after charging of the capacitor is completed, bringing a safety unit into contact with a human body to form an electrified state; and emitting a laser when in the electrified state.

The bringing the safety unit into contact with the human body may include: bringing one hand of a user into contact with a third contact part of the safety unit; and bringing first and second contact parts of the safety unit into contact with a target portion of a body (skin) of the user.

The bringing the safety unit into contact with the body part may include: bringing one hand of a user into contact with a third contact part of the safety unit; bringing the other hand of the user into contact with a body of a patient (another person); and bringing first and second contact parts of the safety unit into contact with a target portion (finger) of the patient.

Advantageous Effects

A laser generating apparatus according to the present invention is configured such that an Er:YAG laser which has a wavelength of 2940 nm and is widely used in the areas of dermatology and dentistry is used and the intensity of laser can be adjusted. Therefore, excessive bleeding can be prevented during blood collection.

Furthermore, the present invention has a reduced size to facilitate carrying and has a safety unit which is operated in such a way as to sense contact between the apparatus and a human body, thus improving the safety for the user and preventing accidents.

BEST MODE

Hereinafter, a first embodiment of the present invention will be described in detail with reference to the attached drawings.

Figure 1:
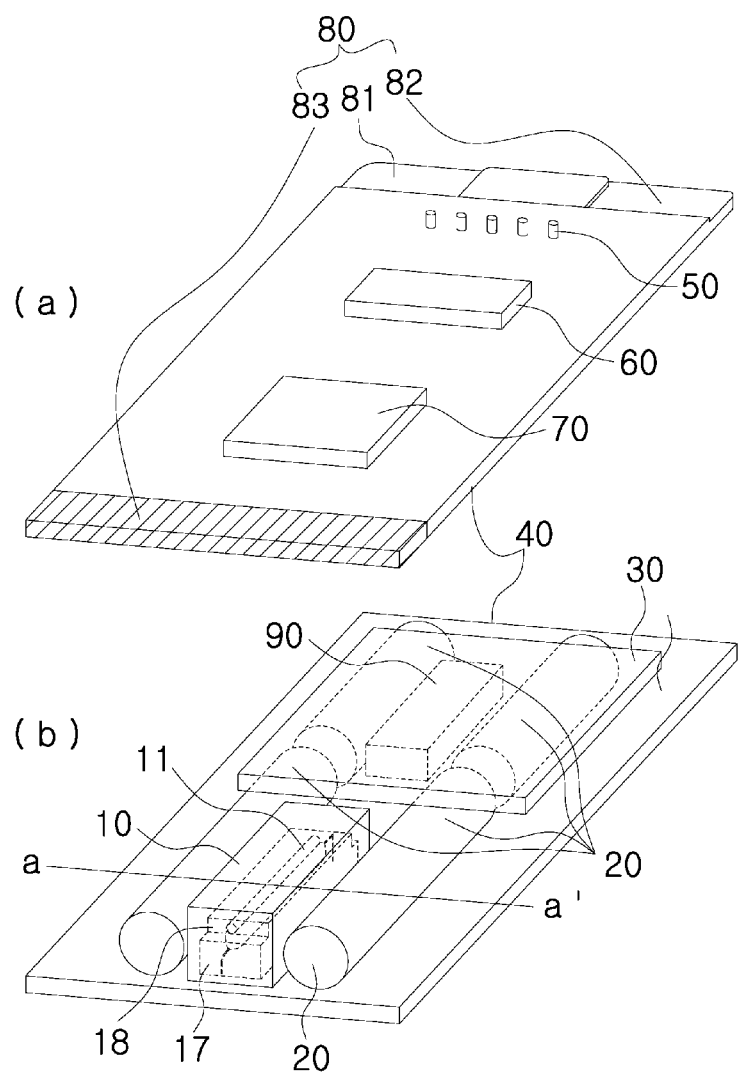
FIGS. 1a and 1b show a front surface and a rear surface of a PCB of a laser generating apparatus according to a first embodiment of the present invention.
Figure 2:
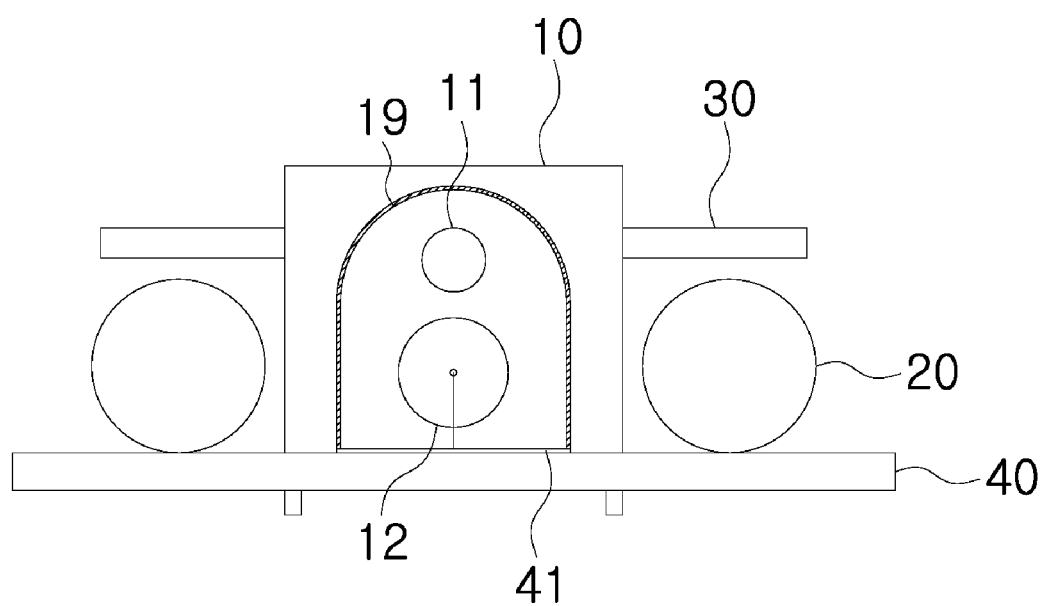
FIG. 2 is a sectional view taken along line a-a' of FIG. 1b.

FIG. 1 is a view illustrating a laser generating apparatus of the present invention. FIG. 2 is a sectional view taken along line a-a' of FIG. 1b. FIGS. 1a and 1b are views showing a laser generating apparatus embodied on a single PCB.

As shown in FIG. 1a, the laser generating apparatus according to the present invention includes, on an upper surface of a PCB 40, a display unit 50, a switch unit 60, a control unit 70 and a safety unit 80.

The display unit 50, the switch unit 60 and the control unit 70 are successively arranged from a first end of the front surface of the PCB 40 to a second end thereof.

The display unit 50 displays a charge state of a battery and a level of laser intensity.

The switch unit 60 includes a power on/off button, laser-intensity-level selection buttons and a laser emission button.

The control unit 70 controls a drive unit 90, a battery 30 and the display unit 50 based on input signals of the switch unit 60 and the safety unit 80.

The safety unit 80 includes a first contact point part 81 and a second contact point part 82 which are respectively disposed on left and right sides of the front end of the PCB 40, and a third contact point part 83 which is provided on a rear end of the PCB 40.

As shown in FIG. 1b, a reflector 10, the drive unit 90, capacitors 20 and the battery 30 are provided on the rear surface of the PCB 40.

An internal space of the reflector 10 includes a first space 17 and a second space 18. A xenon tube 12 is mounted to the PCB 40 in the first space 17 and emits light. A crystal rod 11 is provided in the second space 18. The crystal rod 11 focuses light emitted from the xenon tube 12. Light focused by the crystal rod 11 is amplified, thus making an Er:YAG laser having a wavelength of 2940 nm.

The drive unit 90 is disposed at a predetermined position behind the reflector 10. The capacitors 20 are disposed on opposite sides of the reflector 10 and the drive unit 90. Preferably, two to four capacitors 20 are provided. The battery 30 is disposed over both the drive unit 90 and the capacitors 20 that are provided on the opposite sides of the drive unit 90.

The capacitors 20 are charged by the drive unit 90 that receives power from the battery 30. The charged capacitors 20 apply voltage to the xenon tube 12 so that the xenon tube 12 emits light. The emitted light is focused by the crystal rod 11, thus generating a laser beam.

The crystal rod 11 and the xenon tube 12 which are disposed in the reflector 10 are oriented perpendicular to the surface of the PCB.

Figure 3:
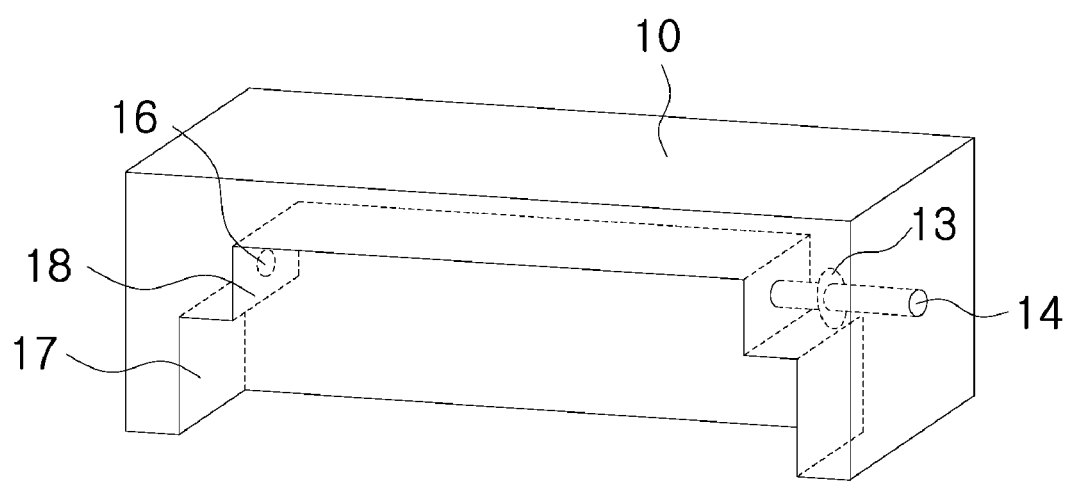
FIG. 3 is a perspective view of a reflector according to the present invention.
Figure 4:
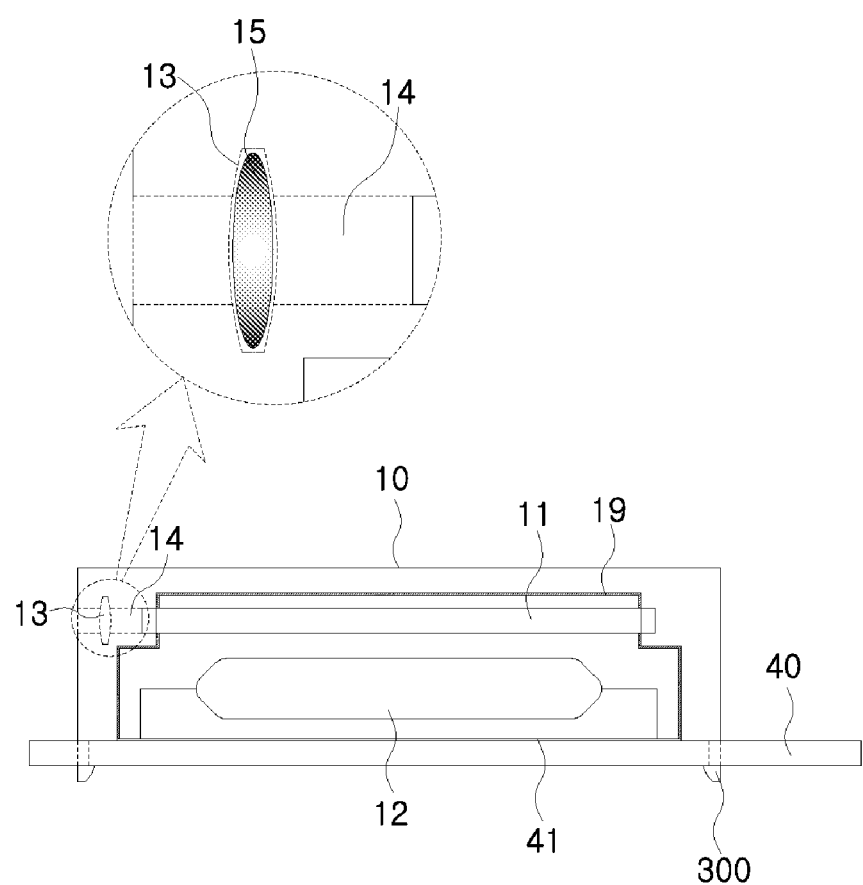
FIG. 4 is a sectional view of the reflector according to the present invention.

FIGS. 3 and 4 are respectively a perspective view and a sectional view illustrating the reflector of the laser generating apparatus according to the first embodiment the present invention.

As shown in FIGS. 3 and 4, the xenon tube 12 is mounted to the PCB 40 and disposed in the first space 17 which is defined in a lower portion of the reflector 10. The crystal rod 11 is inserted into an insert hole 16 in the second space 17 which is defined in an upper portion of the reflector 10. The reflector 10 is mounted to the PCB 40 by bolts or by means of snap coupling designated by reference numeral 300.

The laser generated from the crystal rod 11 is focused to a focusing lens 15 which is installed in a focusing lens installation part 13 and then is emitted through the opening 14. The laser emitted through the opening 14 penetrates the skin of a human body to enable to collect blood. The crystal rod 11, the focusing lens 15 and the opening 14 are coaxially arranged.

An inner surface of the reflector 10 is plated with chrome, as designated by numeral 19, so that light of the xenon tube 12 can be reflected by the inner surface of the reflector 10. The surface of the PCB 40 to which the xenon tube 12 is mounted is plated with gold, as designated by numeral 41, so as to increase reflexibility of light emitted from the xenon tube 12.

Preferably, the reflector 10 has a curved shape having a predetermined radius of curvature or an aspherical surface shape so that light emitted from the xenon tube 12 can be effectively focused to the crystal rod 11. The reflector 10 can have any shape so long as it can increase the reflexibility. Furthermore, the reflector 10 may be formed into an integrated structure, a one-side open structure or a both-sides open structure, as long as the components can be easily installed in the reflector 10 or easily replaced with new ones.

Figure 5:
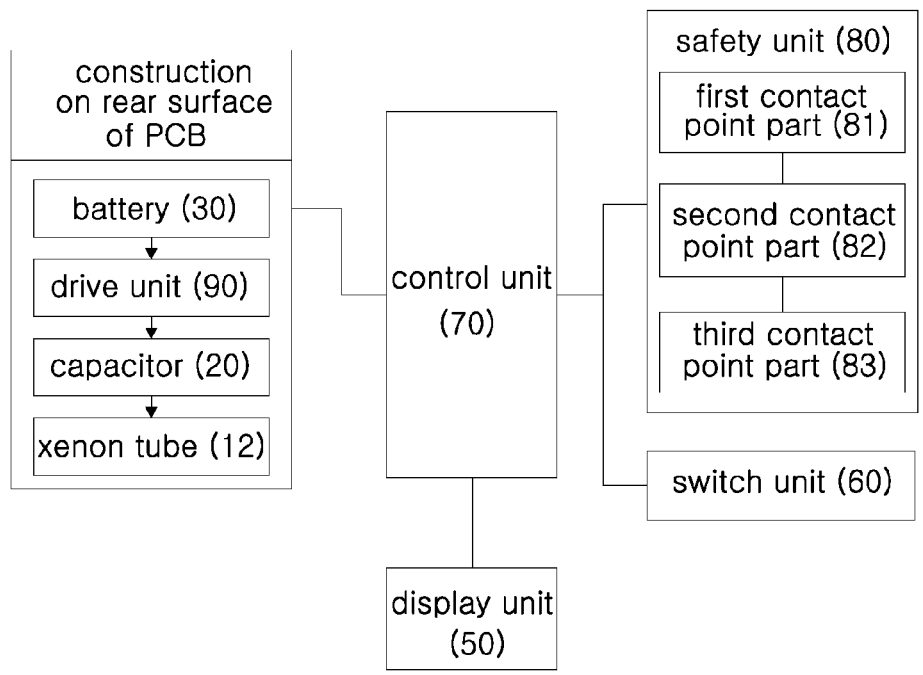
FIG. 5 is a block diagram showing the laser generating apparatus according to the present invention.

FIG. 5 is a block diagram showing the laser generating apparatus according to the present invention.

As shown in FIG. 5, the control unit 70 of the laser generating apparatus according to the present invention controls the safety unit 80, the switch unit 60 and the display unit 50.

The control unit 70 controls the apparatus such that when power is turned on, the battery 30 applies power to the drive unit 90. The drive unit 90 that has received power charges the capacitors 20.

Furthermore, when the intensity of laser is adjusted by the switch unit 60, the control unit 70 controls the display unit 50 such that the intensity of laser and the charge state of the capacitors 20 are displayed on the display unit 50.

After the charging of the capacitor 20 has been completed and the adjustment in the intensity of laser using the switch unit 60 has been completed, the control unit 70 controls the general operation of the laser generating apparatus in such a way that whether parts of the human body makes contact with the first through third contact point parts 81, 82 and 83 of the safety unit 80 is verified, and if there is nothing wrong, the laser emission button of the switch unit 60 is operated to emit a laser.

Figure 6:
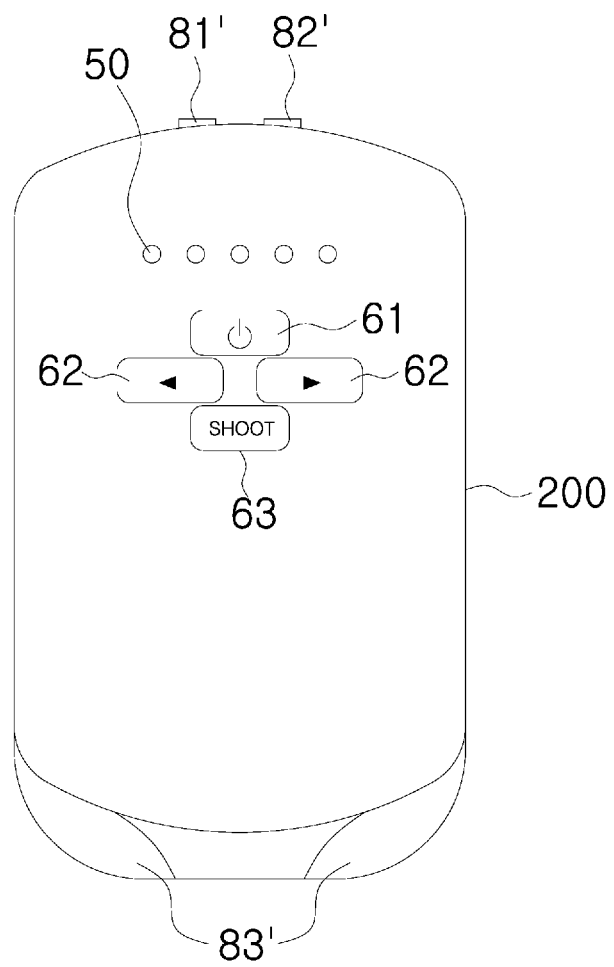
FIG. 6 is a view showing an upper surface of a casing of the laser generating apparatus according to the present invention.

FIG. 6 is a view showing an upper casing of the laser generating apparatus according to the present invention. A lower casing is omitted.

As shown in FIG. 6, the display unit 50 which displays the charge state and the level of laser output is provided at a predetermined position on the upper surface of a casing 200. The display unit 50 is embodied by any one selected from among LEDs, an LCD and an OLED.

A first contact part 81' and a second contact part 82' are provided on left and right sides of a front end of the casing 200. A third contact part 83' is provided on a rear end of the casing 200. The first through third contact parts 81', 82' and 83' respectively make contact with the first through third contact point parts 81, 82 and 83.

Furthermore, provided are a power or cancel button 61 which makes contact with the switch unit 60 of FIG. 1a and is used to operate the laser generating apparatus or cancel the operation command, left/right section buttons 62 which are used to adjust the intensity of laser, and a laser emission button 63 which is used for blood collecting.

The laser generating apparatus of the present invention is used in such a way that the user makes contact with the third contact part 83' and brings the first and second contact parts 81' and 82' into contact with a part of the body to be involved with blood collection. Thereafter, the user pushes the laser emission button 63 to emit a laser. If even any one among the first through third contact parts 81' 82' and 83' does not make contact with the body part, a laser is not emitted.

When conducting the blood collection, to sense current that flows through the body of the user, one hand of the user makes contact with the third contact part 83', and the first and second contact parts 81' and 82' must be brought into contact with a portion of the body to be involved with the blood collection. Only in this case can the laser generating apparatus be operated.

Meanwhile, when it is desired for the user to collect blood of a person, one hand of the user makes contact with the third contact part 83', and the other hand makes contact with a body part (the skin), for example a finger, of the target person before the first and second contact parts 81' and 82' are brought into contact with a blood collection involved portion of the target person. Only in this state can the laser generating apparatus be operated.

Therefore, the laser generating apparatus of the present invention can ensure safety and be prevented from being used wrongly.

Figure 7:
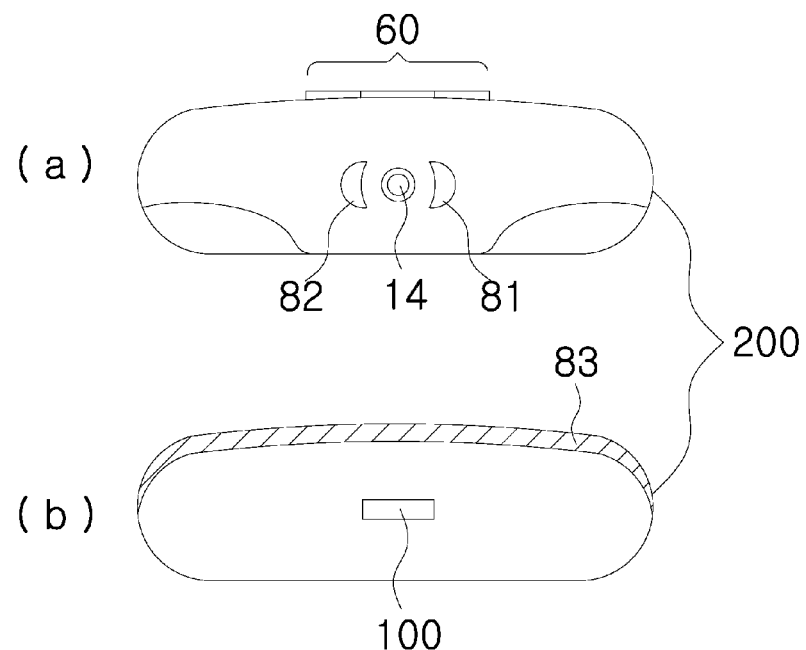
FIG. 7 is a view showing a front surface of the casing of the laser generating apparatus according to the present invention.

FIGS. 7a and 7b are views respectively showing a front surface and a rear surface of the casing of the laser generating apparatus according to the first embodiment of the present invention.

As shown in FIGS. 7a and 7b, the first contact part 81' and the second contact part 82' are provided on left and right sides of the opening 14 in the front surface of the casing 200. A charging jack connector 100, which is used when the battery 30 is charged, is provided in the rear surface of the casing 200. The charging jack connector 100 is embodied by a charging terminal which can be connected to a TTA (standard 34 pins, 20 pins or 5 pins) or USB type charger or the like.

Hereinafter, a second embodiment of the present invention will be described in detail with reference to the attached drawings.

Figure 8:
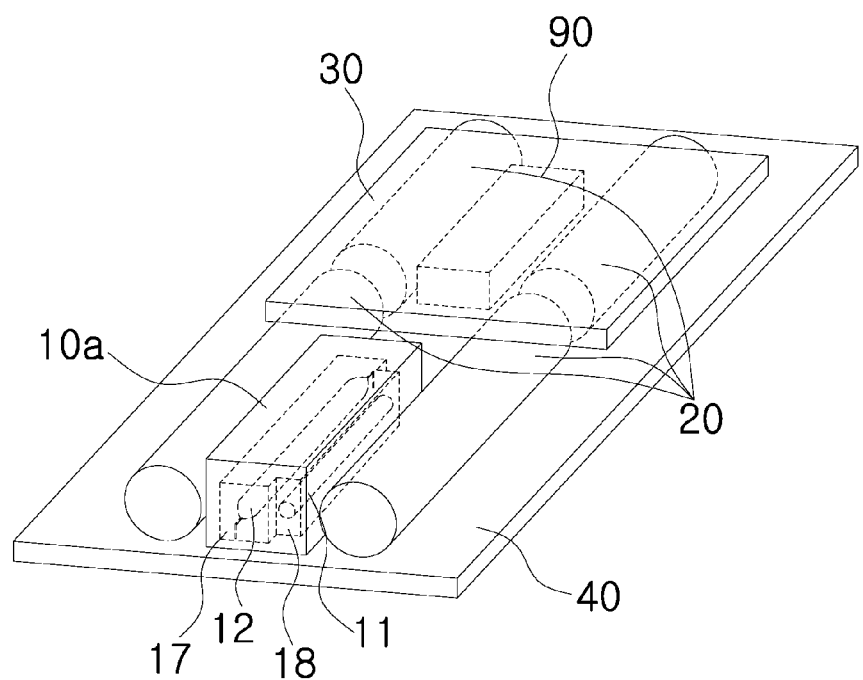
FIG. 8 is a view showing a rear surface of a PCB of a laser generating apparatus according to a second embodiment of the present invention.

FIG. 8 is a view showing a rear surface of a PCB of a laser generating apparatus according to a second embodiment of the present invention.

As shown in FIG. 8, although the general construction of the rear surface of the PCB according to the second embodiment of the present invention is the same as that of the first embodiment shown in FIG. 1b, only the shape of the reflector 10a is different between the first embodiment and the second embodiment.

In this embodiment, the xenon tube 12 and the crystal rod 11 are horizontally provided in the first space 17 and the second space of the reflector 10a. The xenon tube 12 is connected to the PCB 40.

The second embodiment of the present invention is advantageous in that the thickness thereof can be reduced compared to the case of the first embodiment, and the area of a gold-plated portion of the PCB 40 on which the xenon tube 12 is mounted is comparatively large so that a large quantity of light can be reflected.

Figure 9:
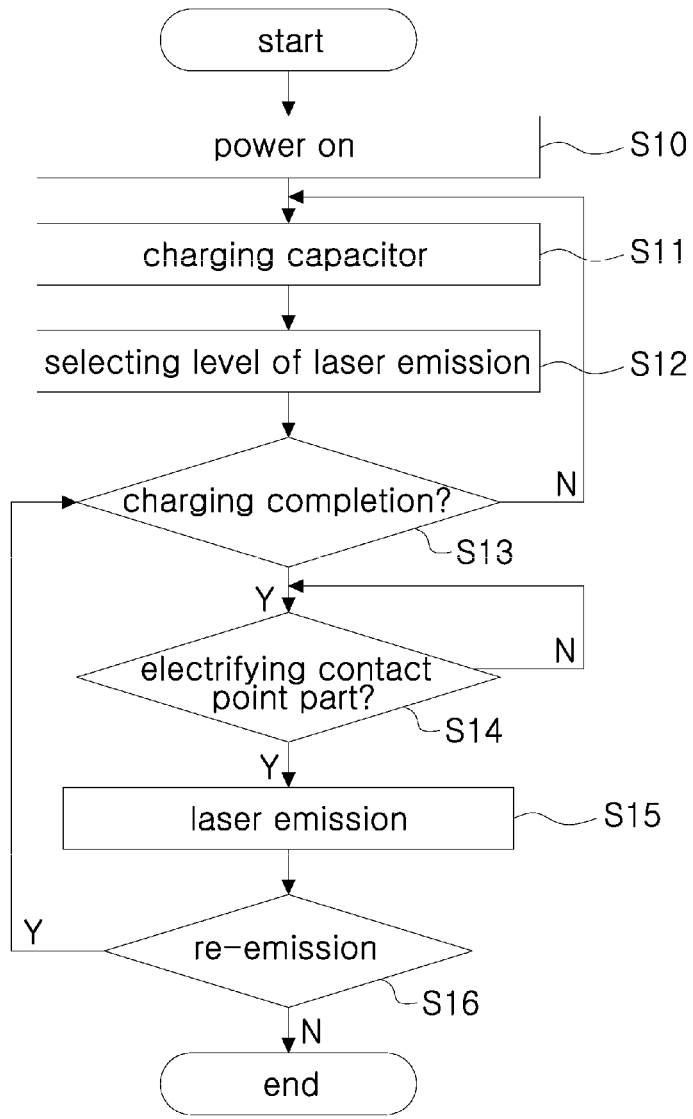
FIG. 9 is a flowchart showing a method of generating laser according to the present invention.

FIG. 9 is a flowchart showing a method of generating laser according to the present invention.

As shown in FIG. 9, in the laser generating method, at step S10, the laser generating apparatus is turned on. When the power is turned on, the capacitors 20 are charged by the drive unit 90, at step S11. While the capacitors 20 are being charged, the level of laser intensity is selected to adjust the intensity of laser, at step S12.

At step S13, the charge state of the capacitor 20 is checked by means of the display unit 50. If the charging is completed, the first through third contact parts 81', 82' and 83' of the safety unit 80 are brought into contact with body parts of the user so that current can flow between the apparatus and the body, at step S14. Thereafter, at step S15, the laser emission button 63 is pressed to emit a laser. If a laser is not emitted or it is required to re-emit a laser, the charge state of the capacitors 20 is checked, and when the charging is completed, a laser is re-emitted, at step S16.

Here, making current flow may be achieved by bringing one hand of the user into contact with the third contact part 83' and bringing the first and second contact parts 81' and 82' of the safety unit 80 into contact with a target portion of the body part such as the skin, a finger, etc. to be involved with blood collection.

Alternatively, making current flow may be achieved by bringing one hand of the user into contact with the third contact part 83', bringing the other hand of the user into contact with the body of a target person, and then bringing the first and second contact parts 81' and 82' of the safety unit 80 into contact with a target portion of the body part such as the skin, a finger, etc. of the target person.

As described above, in a laser generating apparatus according to the present invention, an Er:YAG laser having a wavelength of 2940 nm is used so that it is almost harmless to the human body. Furthermore, the present invention makes it possible for patients who suffer from diabetes to overcome the pain and fear of lancing the body with a needle to collect blood several times (three or more times) a day. Moreover, the present invention can solve a problem of secondary infection which may be caused when a needle is replaced with a new one or a needle that has been used for a patient is reused for another patient. The output of a laser can be controlled by adjusting the level of the laser intensity so that excessive bleeding can be prevented.

In addition, the laser generating apparatus can be used not only for diabetic patients but also for collecting a blood sample for a blood test. The apparatus can collect only an appropriate amount of blood required for the blood test. Furthermore, because the temperature of laser is very high, for example, is 1000° C. or more, sterilizing effect can be provided so that a lanced portion can be prevented from being infected by bacteria.

Although the preferred embodiments of the present invention have been disclosed, those skilled in the art will appreciate that various modifications, additions and substitutions are possible, without departing from the scope and spirit of the invention. Therefore, the embodiments disclosed in this specification are only for illustrative purposes rather than limiting the technical spirit of the present invention. The scope of the present invention must be defined by the accompanying claims, and all technical spirits that are in the equivalent range to the claims must be regarded as falling within the scope of the present invention.

The invention claimed is:

1. An apparatus for generating a laser, comprising:
   on an upper surface of a printed circuit board,
     a display unit displaying a battery charge state and an intensity of a laser;
     a switch unit provided to turn power on/off, adjust the intensity of the laser and control emission of the laser;
     a safety unit comprising first through third contact point parts, wherein the first through third contact point parts respectively contact a body surface as a precondition for generating the laser; and
     a control unit controlling the drive unit and the display unit, and
   on a lower surface of the printed circuit board,
     a reflector having a first space and a second space therein;
     a xenon tube emitting light in the first space;
     a crystal rod amplifying the light in the second space and generating a laser;
     a focusing lens focusing the laser and forming a focus;
     a focusing lens installation part in which the focusing lens is installed; a capacitor applying voltage to the xenon tube;
     a drive unit charging the capacitor; and
     a battery supplying power to the drive unit.

2. The apparatus according to claim 1, wherein the xenon tube and the crystal rod are provided in the reflector and oriented perpendicular to or parallel to the rear surface of the printed circuit board.

3. The apparatus according to claim 1, wherein an inner surface of the reflector is plated with chrome.

4. The apparatus according to claim 1, wherein the printed circuit board in contact with an inner surface of the reflector is plated with gold.

5. The apparatus according to claim 1, wherein the display unit is embodied by at least one selected from among an LED, an LCD and an OLED.

6. The apparatus according to claim 1, wherein the first through third contact point parts of the safety unit respectively make contact with first through third contact parts of a casing.

7. The apparatus according to claim 1, wherein the switch unit comprises: a power button used to turn on or off the laser generating apparatus; a selection button used to select a level of laser intensity; and a laser emission button used to conduct blood collection.

8. The apparatus according to claim 6, wherein blood collection is conducted in such a way that one hand of a user makes contact with the third contact part, and the first and second contact parts are brought into contact with a target portion of a body (skin) of the user.

9. The apparatus according to claim 6, wherein blood collection is conducted in such a way that one hand of a user makes contact with the third contact part, the other hand of the user makes contact with a body of a patient (another person), and the first and second contact parts are brought into contact with a target portion of the body of the patient.

10. The apparatus according to claim 6, further comprising, on a rear surface of the casing, a charging jack connector used to charge the battery.

* * * * *